US008486648B2

(12) United States Patent
Livingston et al.

(10) Patent No.: US 8,486,648 B2
(45) Date of Patent: Jul. 16, 2013

(54) METHODS OF DETECTING OVARIAN CANCER

(75) Inventors: David Livingston, Brookline, MA (US); Ronny Drapkin, Newton, MA (US)

(73) Assignee: Dana-Farber Cancer Institute, Inc., Boston, MA (US)

(*) Notice: Subject to any disclaimer, the term of this patent is extended or adjusted under 35 U.S.C. 154(b) by 1251 days.

(21) Appl. No.: 11/883,103

(22) PCT Filed: Feb. 16, 2006

(86) PCT No.: PCT/US2006/005665
§ 371 (c)(1), (2), (4) Date: Jun. 19, 2008

(87) PCT Pub. No.: WO2006/089125
PCT Pub. Date: Aug. 24, 2006

(65) Prior Publication Data
US 2008/0286199 A1    Nov. 20, 2008

Related U.S. Application Data

(60) Provisional application No. 60/653,410, filed on Feb. 16, 2005.

(51) Int. Cl.
| | |
|---|---|
| C12Q 1/00 | (2006.01) |
| G01N 1/00 | (2006.01) |
| G01N 21/00 | (2006.01) |
| G01N 21/75 | (2006.01) |
| G01N 33/00 | (2006.01) |
| G01N 33/48 | (2006.01) |
| G01N 33/53 | (2006.01) |
| G01N 33/567 | (2006.01) |
| G01N 33/574 | (2006.01) |

(52) U.S. Cl.
USPC .............. 435/7.23; 435/4; 435/7.1; 435/7.21; 435/7.72; 435/7.92; 436/63; 436/64; 436/164; 436/166; 436/174; 436/501

(58) Field of Classification Search
USPC ..... 435/4, 7.1, 7.21, 7.23, 7.72, 7.92; 436/63, 436/64, 164, 166, 174, 501
See application file for complete search history.

(56) References Cited

U.S. PATENT DOCUMENTS

| | | | |
|---|---|---|---|
| 4,230,767 A | 10/1980 | Isaka et al. ................ 428/349 |
| 4,233,402 A | 11/1980 | Maggio et al. ............... 435/7 |
| 4,275,149 A | 6/1981 | Litman et al. ................ 435/7 |
| 4,376,110 A | 3/1983 | David et al. ................ 436/513 |
| 4,659,678 A | 4/1987 | Forrest et al. ............. 436/512 |
| 4,727,022 A | 2/1988 | Skold et al. ................... 435/7 |
| 2005/0176002 A1* | 8/2005 | Diamandis et al. ........... 435/6 |

OTHER PUBLICATIONS

Pfundt et al. Constitutive and Inducible Expression of SKALP/Elafin Provides Anti-Elastase Defense in Human Epithelia (J. Clin. Invest. 98(6): 1389-1399, Sep. 1996).*

Pfundt et al. Constitutive and inducible expression of SKALP/Elafin provides anti-elastase defense in human epithelia. J. Clin. Invest. 98(6): 1389-1399, Sep. 1996.*

Scheuer, Lauren et al. Outcome of preventive surgery and screening for breast and ovarian cancer in BRCA mutation carriers. Journal of Clinical Oncology 20(5): 1260-1268, Mar. 1, 2002.*

Bingle et al. The putative ovarian tumour marker gene HE4 (WFDC2), is expressed in normal tissues and undergoes complex alternative splicing to yield multiple protein isoforms. Oncogene 21: 2768-2773, 2002.*

Ashcroft et al., "Secretory leukocyte protease inhibitor mediates non-redundant functions necessary for normal wound healing", *Nat. Med.*, 6(10):1147-1153 (2000).

Bast et al., "Humoral markers for epithelial ovarian carcinoma", in *Ovarian Malignancies: Diagnostic and Therapeutic Advances*, M. Piver, Ed., Edinburgh, London, pp. 11-25 (1987).

Devoogdt et al., "Secretory leukocyte protease inhibitor promotes the tumorigenic and metastatic potential of cancer cells", *Proc. Natl. Acad. Sci. U.S.A.*, 100(10):5778-5782 (2003).

Drapkin et al., "Human epididymis protein 4 (HE4) is a secreted glycoprotein that is overexpressed by serous and endometrioid ovarian carcinomas", *Cancer Res.*, 65(6):2162-2169 (2005).

Genbank Accession No. AAA36483, Feb. 11, 2002.
Genbank Accession No. AAB26371, Jul. 23, 1993.
Genbank Accession No. AAB34627, May 17, 2002.
Genbank Accession No. BAA02441, Jul. 21, 2005.
Genbank Accession No. CAA79223, Oct. 7, 2008.
Genbank Accession No. JH0614, Aug. 17, 1992.
Genbank Accession No. NP_002629, Mar. 29, 2009.
Genbank Accession No. NP_003055, Jun. 7, 2009.
Genbank Accession No. P19957, Jun. 16, 2009.

Hellstrom et al., "The HE4 (WFDC2) protein is a biomarker for ovarian carcinoma", *Cancer Res.*, 63:3695-3700 (2003).

Kluger et al., "Using a xenograft model of human breast cancer metastasis to find genes associated with clinically aggressive disease", *Cancer Res.*, 65(13):5578-5587 (2005).

O'Marcaigh et al., "Estimating the predictive value of a diagnostic test, how to prevent misleading or confusing results", *Clin. Ped.*, 32(8):485-491 (1993).

Scully, R.E., "Pathology of ovarian tumors" in *Ovarian Malignancies; Diagnostic and Therapeutic Advances*, M. Piver, Ed., Edinburgh, London, p. 28 (1987).

Shultz, E.K., "Clinical interpretation of laboratory procedures" in Teitz, *Fundamentals of Clinical Chemistry*, Burtis and Ashwood (Eds.), 4th Ed., W.B.Saunders Co., Philadelphia, PA, pp. 192-199 (1996).

Tsukishiro et al., "Use of serum secretory leukocyte protease inhibitor levels in patients to improve specificity of ovarian cancer diagnosis", *Gynecol. Oncol.*, 96(2):516-519 (2005).

Vandermeeren et al., "Development and application of monoclonal antibodies against SKALP/elafin and other trappin family members", *Archives Dermatological Res.*, 293(7):343-349 (2001).

Zweig et al., "ROC curve analysis: An example showing the relationships among serum lipid and apolipoprotein concentrations in identifying patients with coronary artery disease", *Clin. Chem.*, 38(8):1425-1428 (1992).

* cited by examiner

*Primary Examiner* — Alana Harris Dent
(74) *Attorney, Agent, or Firm* — Mintz Levin Cohn Ferris Glovsky and Popeo, P.C.; Ivor R. Elrifi; Cynthia A. Kozakiewicz

(57) ABSTRACT

The present invention provides methods of detecting ovarian cancer using biomarkers.

33 Claims, 7 Drawing Sheets

METHODS OF DETECTING OVARIAN CANCER

RELATED APPLICATIONS

This application is a national stage application, filed under 35 U.S.C. §371, of International Application No. PCT/US2006/005665, filed on Feb. 16, 2006 which claims the benefit of U.S. Ser. No. 60/653,410, filed Feb. 16, 2005.

INCORPORATION-BY-REFERENCE OF SEQUENCE LISTING

The contents of the text file named "20363-032NATL_ST25.txt", which was created on Jul. 18, 2012 and is 3 KB in size, are hereby incorporated by reference in their entirety.

FIELD OF THE INVENTION

The invention relates to generally to the early detection of ovarian cancer.

BACKGROUND OF THE INVENTION

Carcinoma of the ovary kills more women in North America and Europe than all other gynecological malignancies combined. Worldwide, the incidence is estimated to include 190,000 new cases and 114,000 deaths annually. Despite advances in surgical approaches and chemotherapeutic agents, ovarian cancer has the third lowest survival rate out of 11 different organ categories. In the United States it is the fourth most frequent cause of cancer death among women. Of all females born in the United States, one of every 70 will develop ovarian cancer and one of every 100 will die from this disease. Unfortunately, the vast majority of patients are diagnosed at an advanced clinical stage where the average 5-year survival is 30%. Fortuitous detection of early stage tumors is associated with a substantial increased 5-year survival (>95%). Therefore, early detection could significantly impact long-term survival.

Currently, cancer antigen 125 (CA-125) is the most widely used serum biomarker for ovarian cancer. Serum concentrations of CA-125 are elevated (>35 U/ml) in 75-80% of patients with advanced-stage disease and this marker is routinely used to follow response to treatment and disease progression in patients from whom CA-125-secreting tumors have been resected. However, because the levels of CA-125 are correlated with tumor volume, only 50% of patients with early-stage disease have elevated levels, indicating that the sensitivity of CA-125 as a screening tool for early stage disease is limited. The utility of CA-125 screening is further limited by the high frequency of false-positive results associated with a variety of benign conditions, including endometriosis, pregnancy, menstruation, pelvic inflammatory disease, peritonitis, pancreatitis, and liver disease. Hence, there has long been a need for a means of detecting ovarian cancer at an early stage and for an ovarian cancer monitoring supplemental to CA-125.

SUMMARY OF THE INVENTION

The invention provides biological markers to monitor the diagnosis and prognosis of Mullerian-derived tumors.

Mullerian-derived cancers (e.g., ovarian, endometrial, fallopian tube, endocervical cancers) are diagnosed in a subject by detecting an Elafin polypeptide in a sample obtained from the subject. The presence of an Elafin polypeptide in the sample indicate the presence of a Mullerian-derived tumor in the subject. Whereas, the absence of an Elafin polypeptide in the sample indicates the absence of a Mullerian-derived tumor in the subject. Optionally, the level of the Elafin polypeptide in the subject is compared to a control (i.e. standard) value. A higher level of Elafin in the test sample compared to the control sample indicates mullerian-derived cancer in the subject. By higher level is meant at least a 2, 4, 5, 10-fold or higher value in the test sample compared to the control sample The progression of a Mullerian-derived cancer is monitored by detecting an Elafin polypeptide in two or more samples obtained from a subject over time and comparing the amount of Elafin polypeptide detected. For example, a first sample is obtained prior to the subject receiving treatment and one or more subsequent samples are taken after or during treatment of the subject. The cancer is progressing if the amount of Elafin polypeptide increases over time. Whereas the cancer is not progressing in the amount of Elafin polypeptide remains constant or decreases over time.

The sample is a biological sample obtained from the subject. The sample is for example, serum, blood plasma, ascites fluid, urine, a vaginal secretion or a tissue biopsy.

A full length Elafin polypeptide is detected. Alternatively, a fragment of the Elafin polypeptide is detected. The Elafin polypeptide has a molecular weight of 12.3 kD, 9.9 kD or 6.0 kD. The Elafin polypeptide is detected by any means known in the art. The Elafin polypeptide is detected electrophoretically or immunochemically. Immunochemical detection includes for example, radio-immunoassay, immunofluorescence assay, or enzyme-linked immunosorbant assay. For example, an Elafin polypeptide is detected using an anti-Elafin antibody and the amount of antigen-antibody complex is detected as a measure of Elafin in the sample.

Mullerian-derived cancers include ovarian cancer, endocervical cancer, fallopian cancer or uterine cancer. Ovarian cancer includes serous, endometroid, mucinous, clear cell or transitional type cancers.

The method may be carried out on a subject concurrently with testing that patient for elevated CA-125, HE4 or SLPI levels, with the combined results providing a superior indication of the presence of cancer than screening or monitoring with Elafin alone. The subject has not been previously diagnoses as having cancer. Alternatively, the subject has been diagnosed with cancer, e.g. ovarian cancer. Optionally, the subject has been previously treated surgically or hormonally for cancer. The subject is positive for the BRCA1 or BRCA2 gene.

Also included in the invention are method of alleviating a symptom of a mullerian-derived tumor in a subject by administering to a subject an anti-Elafin antibody linked to a toxin. The toxin is for example, a chemotherapeutic agent, a radionuclide, a ricin A chain polypeptide, a cholera toxin polypeptide, or a pertussis toxin polypeptide.

Kits containing in one or more containers, an Elafin antibody, a detection reagent and instructions are further provides by the invention.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIG. 8 is a photograph of a Western blot showing that SLPI is secreted by ovarian cancer cell lines.

FIG. 9 is a series of photographs showing that Elafin is expressed by human ovarian cancers.

DETAILED DESCRIPTION OF THE INVENTION

The invention is based upon the discovery of biomarkers for early detection (e.g., Stage I, or Stage II) ovarian cancer. Using cDNA microarray analysis and RT-PCR, it was determined that two WAP domain proteins, HE4 and SLPI were significantly overexpressed in ovarian carcinomas. Additional studies revealed that a third WAP protein, Elafin, is also expressed by ovarian carcinomas and its expression parallels that of HE4. Both HE4 and Elafin, while overexpressed in ovarian carcinoma, are not expressed in immortalized ovarian surface epithelial cells, and thus are ideal candidate markers of ovarian cancer. Accordingly, the invention provides methods of detecting and evaluating ovarian cancer in a subject by evaluating Elafin expression. The methods disclosed herein are employed with subjects suspected of carrying cancer, to monitor subjects who have been previously diagnosed as carrying cancer, and to screen subjects who have not been previously diagnosed as carrying cancer.

Figure 5A:
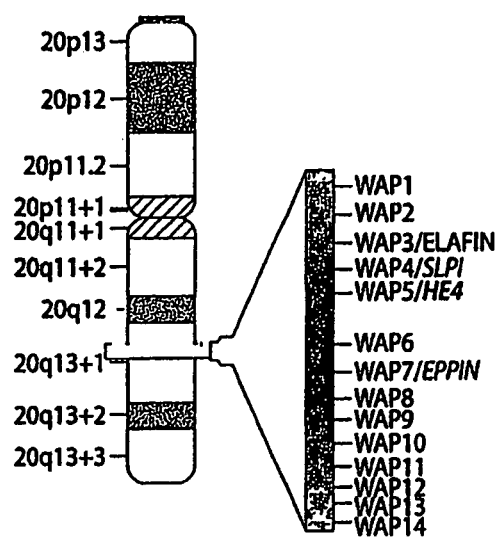
FIG. 5A is an illustration showing the WAP gene cluster.
Figure 5B:
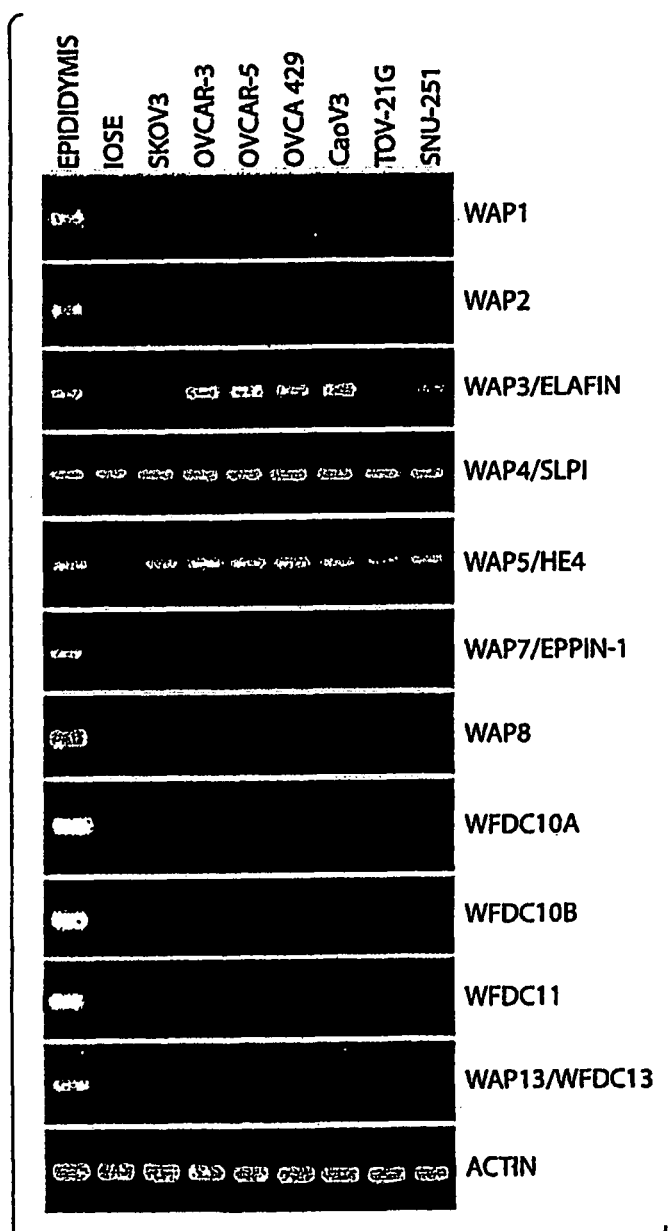
FIG. 5B is a photograph of RT-PCR expression data of the entire WAP cluster in various ovarian carcinoma cell lines versus epididymis (positive control) and IOSE (negative control). These data show that only Elafin, HE4, and SLPI are expressed in ovarian cancers.
Figure 6:
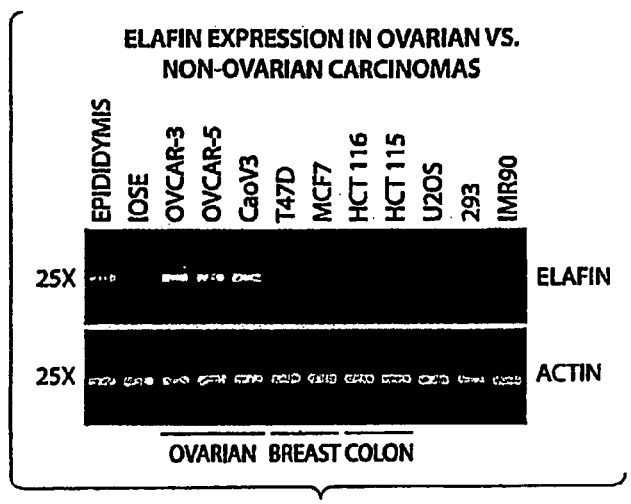
FIG. 6 is a photograph of RT-PCR expression of Elafin in ovarian (OVCAR-3, -5, CaoV3) versus non-ovarian (MCF7, T47D, HCT-115, -116, U20S, IMR90) cell lines. Actin serves as a loading control.
Figure 7:
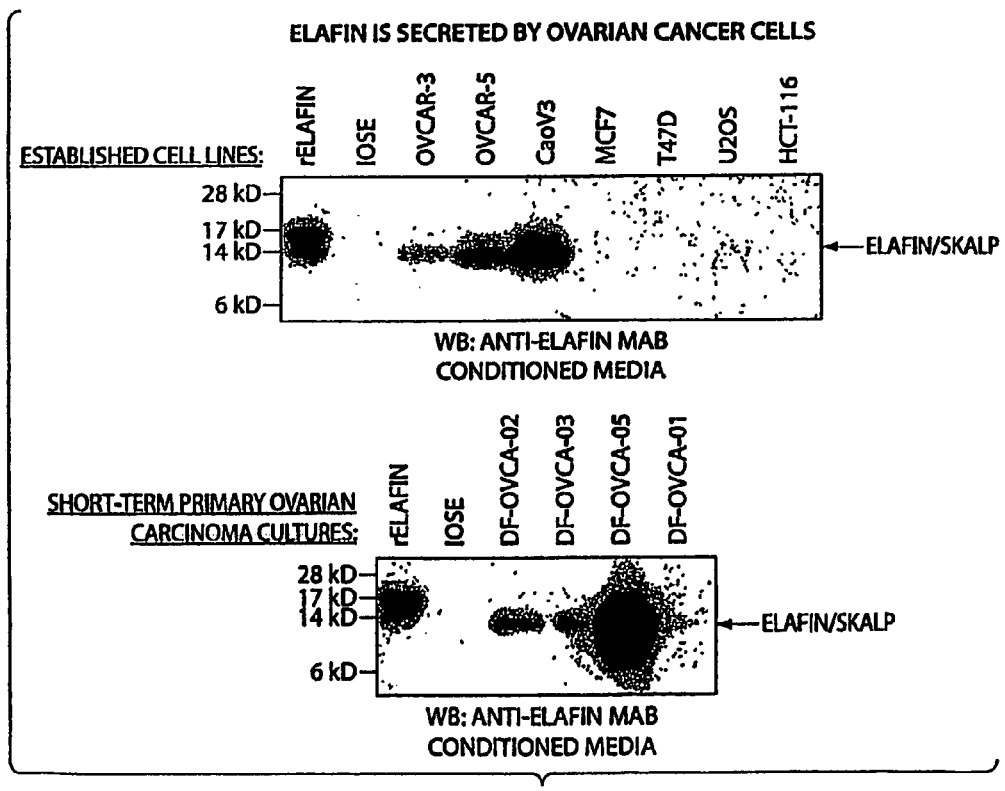
FIG. 7 shows two photographs of Western Blots. The top Western Blot shows that Elafin is secreted by established ovarian cancer cells. The bottom Western Blot shows that Elafin is secreted by primary ovarian carcinoma cultures isolated from ascites fluid patients with ovarian cancer.

It has been previously reported that HE4, a member of the WAP cluster on chromosome 20q13, is overexpressed and secreted by ovarian carcinomas (Hellstrom et al., Cancer Res 2003; 63: 3695-700; Drapkin et al., Cancer Res 2005 65: 2162-9). To determine whether other members of the WAP cluster (FIG. 1A) are also overexpressed and secreted by ovarian carcinomas, the expression profile of the WAP cluster was examined in seven ovarian cancer cell lines and two lines of human ovarian surface epithelium (the cell of origin) by RT-PCR. The analysis revealed that three members of the WAP cluster are expressed by these tumor cells: Elafin, SLPI, and HE4 (FIG. 5B). Analysis of non-ovarian tumors revealed that Elafin expression is unique to ovarian carcinomas (FIG. 6). The Elafin gene predicts a polypeptide with a signal sequence that is likely required for the secretion of the protein. Western blot analysis of conditioned media from ovarian cancer cell lines showed that the Elafin protein is secreted by these tumor cells and not by breast, colon or bone cancer cells (FIG. 7, top panel). To rule-out the possibility that this observation is non-specific and related to the effects of long-term culture, primary ovarian carcinoma cells were purified from ascites fluid of women with ovarian cancer. Western blot analysis revealed that these primary tumors also secreted Elafin into the extracellular environment (FIG. 7, bottom panel). Using affinity-purified antibodies against full-length Elafin, formalin-fixed paraffin embedded sections of human ovarian carcinomas were examined for Elafin expression. Elafin was readily detected in a subpopulation of tumor cells and not in the surrounding stromal or inflammatory cells (FIG. 9). Therefore, like HE4, Elafin is expressed and secreted by ovarian carcinoma cells and is a good candidate for diagnostic, therapeutic, and serological assays.

Elafin

Figure 1A:
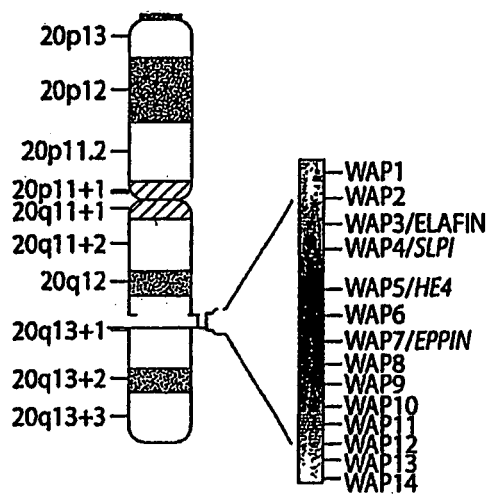
FIG. 1A is an illustration depicting the region on chromosome 20q13 that harbors the WAP gene cluster, including HE4, SLPI, Eppin-1, and Elafin.

Elafin is an epithelial proteinase inhibitor also known as Skin-derived Anti-leukoproteinase (SKALP) and Elastase-Specific Inhibitor (ESI). The Elafin gene resides within a 700-kilobase locus on chromosome 20q13 that contain fourteen genes encoding whey acidic protein (WAP) domain proteins (FIG. 1A). Elafin itself is a WAP domain containing protein. Elafin belongs to the Trappin gene family and was given the systematic name Trappin-2 in a recent classification. The Trappin family is defined by an N-terminal transglutaminase substrate domain and a C-terminal four disulphide core. Trappins have been suggested to play a role in the regulation of inflammation and in protection against tissue damage in stratified epithelia. Elafin is an inhibitor of leukocyte elastase and proteinase-3 and in addition it is a substrate for transglutaminases. The protein is constitutively expressed in various epithelia including those of hair follicles, esophagus, vagina and oral cavity. Elafin is not present in normal human skin but is strongly induced in inflammatory conditions like psoriasis and wound healing. The full-length protein is translated as a 12.3 kDa protein of 117 amino acids termed pre-Elafin or Trappin-2. Cleavage of the signal peptide yields a mature protein with a molecular mass of 9.9 kDa. The 9.9 kDa secreted protein is the major form found in culture medium. In skin extracts a 6 kDa form comprising the 57 most C-terminal amino acids is present. In serum, both the 9.9 and the 6 kDa form appear to be present. In serum/plasma of healthy individual approximately 10-50 ng/mL of Elafin is present. Elafin is abundantly expressed in ovarian carcinomas but absent in IOSE cells. Further, using conditioned media from IOSE cells and a collection of ovarian carcinomas cells it was found that Elafin is secreted into the media by ovarian carcinoma cells but not IOSE cells. Moreover, Elafin was not expresses or secreted by tumor cells from breast, colon, cervical, lung, brain or bone tumor cells.

Suitable sources of Elafin polypeptides are available as GENBANK™ Accession No. AAA36483 (SEQ ID NO:1). This sequence and its corresponding nucleic acid sequence (SEQ ID NO: 2) is illustrated below in Table 1. Other sources include the protein sequences that are shown in GENBANK™ Accession No. NP002629, P19957, NP003055, BAA02441, JH0614, AAB34627, CAA79223 and AAB26371, and are incorporated herein by reference in their entirety. EntrezGene number 5266.

TABLE 1

Elafin Precursor

```
                                                              (SEQ ID NO: 1)
  1 AGGCCAAGCTGGACTGCATAAAGATTGGTATGGCCTTAGCTCTTAGCCAAACACCTTCCT
    ............................................................

61 GACACCATGAGGGCCAGCAGCTTCTTGATCGTGGTGGTGTTCCTCATCGCTGGGACGCTG
    ......-M--R--A--S--S--F--L--I--V--V--V--F--L--I--A--G--T--L-

121 GTTCTAGAGGCAGCTGTCACGGGAGTTCCTGTTAAAGGTCAAGACACTGTCAAAGGCCGT
 19 -V--L--E--A--A--V--T--G--V--P--V--K--G--Q--D--T--V--K--G--R-

181 GTTCCATTCAATGGACAAGATCCCGTTAAAGGACAAGTTTCAGTTAAAGGTCAAGATAAA
 39 -V--P--F--N--G--Q--D--P--V--K--G--Q--V--S--V--K--G--Q--D--K-

241 GTCAAAGCGCAAGAGCCAGTCAAAGGTCCAGTCTCCACTAAGCCTGGCTCCTGCCCCATT
 59 -V--K--A--Q--E--P--V--K--G--P--V--S--T--K--P--G--S--C--P--I-

301 ATCTTGATCCGGTGCGCCATGTTGAATCCCCCTAACCGCTGCTTGAAAGATACTGACTGC
 79 -I--L--I--R--C--A--M--L--N--P--P--N--R--C--L--K--D--T--D--C-

361 CCAGGAATCAAGAAGTGCTGTGAAGGCTCTTGCGGGATGGCCTGTTTCGTTCCCCAGTGA
 99 -P--G--I--K--K--C--C--E--G--S--C--G--M--A--C--G--V--P--Q--*-

(SEQ ID NO: 2)
421 GAGGGAGCCGGTCCTTGCTGCACCTGTGCCGTCCCCAGAGCTACAGGCCCCATCTGGTCC
    ............................................................

481 TAAGTCCCTGCTGCCCTTCCCCTTCCCACACTGTCCATTCTTCCTCCCATTCAGGATGCC
    ............................................................

541 CACGGCTGGAGCTGCCTCTCTCATCCACTTTCCAATAAAGAGTTCCTTCTGCTCC
    ............................................................
```

Secretory Leukocyte Proteinase Inhibitor

Secretory leukocyte proteinase inhibitor (SLPI) is a protein of 12 kDa composed of 2 cysteine-rich domains with a protease inhibitory site situated in the carboxy-terminal domain. SLPI is a potent inhibitor of serine proteases, such as neutrophil elastase, cathepsin G, mast cell chymase, and a chymotrypsin-like enzyme found in the stratum corneum of the skin. In addition to its primary function as an anti-protease, SLPI has also been shown to have multiple functions relevant to innate host defense, including anti-microbial and anti-inflammatory activity, the control of intracellular enzyme synthesis, and the suppression of monocyte matrix metalloproteinase production and activity. Recently, a mouse knockout of SLPI was reported. Absence of SLPI leads to delayed wound healing, an increased and prolonged inflammatory response, enhanced elastase activity, and delayed matrix accumulation (Ashcroft et al., Nature Medicine 2000; 6: 1147-1153). Interestingly, this defect in wound healing in SLPI null resembles the tumor microenvironment. In fact, cancers have often been described at smoldering wounds. In support of this notion SLPI was recently shown to promote the tumorigenic and metastatic potential of cancer cells in vivo (Devoogdt et al., PNAS 2003; 100: 5778-5782; Kluger et al., Cancer Res 2005; 65: 5578-5587) and to be secreted by ovarian cancer cells (FIG. 8) and circulate in the bloodstream of women with this disease (Tsukishiro et al., Gyn Oncol 2005; 96: 516-519).

HE4

Like SLPI and Elafin, the HE4 gene is a member of the WAP cluster on chromosome 20q13. It was first described as a gene specifically expressed in the male epididymis, a property common to all the WAP genes. Microarrays studies subsequently showed that HE4 is commonly overexpressed in ovarian tumors. In order to examine the expression of HE4 in ovarian carcinomas rabbit polyclonal antibodies against full-length human HE4 were developed and used to profile the expression of HE4 protein in normal and malignant tissues. Briefly, it was found that its expression in tumors was restricted to certain histological subtype: 93% of serous and 100% of endometrioid ovarian carcinomas expressed HE4, while only 50% and 0% of clear cell carcinomas and mucinous tumors, respectively, were positive. Tissue microarrays revealed that the majority of non-ovarian carcinomas do not express HE4; consistent with our observation that HE4 protein expression is highly restricted in normal tissue to the reproductive tracts and respiratory epithelium. HE4 is predicted to encode a secreted protein. Using RT-PCR ovarian cancer cell lines were identified that endogenously over-express HE4. Culture media from these cells contained a secreted form of HE4 that is N-glycosylated (Drapkin et al., Cancer Res 2005; 65: 2162-9). This observation is consistent with the recent report that HE4 circulates in the bloodstream of patients with epithelial ovarian carcinomas (Hellstrom et al., Cancer Res 2003; 63: 3695-700). Therefore, HE4 is a secreted glycoprotein that is overexpressed by serous and endometrioid epithelial ovarian carcinomas.

Diagnostic and Therapeutic Methods

Mullerian-derived tumors are detected by examining the expression an Elafin polypeptide from a test population of cells (i.e., a patient derived tissue sample). Mullerian-derived tumors include for example, ovarian cancer, endocervical cancer, fallopian cancer, or uterine cancer. A tissue sample is for example, a biopsy tissue, scrapings, or ovarian tissue removed during surgery. Preferably, the test cell population comprises a cell obtained from the female reproductive system. For example, the cell is an ovarian cell, a uterine cell, a vaginal cell, or a fallopian cell. Expression of Elafin is also measured in blood, serum, acsites fluid, urine, vaginal secretion or other bodily fluids.

Expression of an Elafin polypeptide is determined in the test sample and compared to the expression of the normal control level. By normal control level is meant the expression level of Elafin typically found in a population not suffering from a mullerian derived tumor. The normal control level can be a range or an index. Alternatively, the normal control level can be a database of expression patterns from previously tested individuals. An increase of the level of expression in the patient derived sample of Elafin indicates that the subject is suffering from or is at risk of developing a mullerian derived tumor. Optionally, expression of other biomarkers for a particular cancer are also determined as further indication of whether or not the subject is carrying a cancer. For example, SLPI, HE4 or CA-125 is detected. As noted above, elevated levels of CA-125 antigen is the current serum marker for ovarian cancer, particularly epithelial ovarian cancer. CA-125 is detected in any suitable manner, but is typically detected by contacting a sample from the patient with an antibody which binds CA-125 and then detecting the presence or absence of a reaction product. The antibody may be monoclonal, polyclonal, chimeric, or a fragment of the forgoing, as discussed in detail above, and the step of detecting the reaction product may be carried out with any suitable immunoassay. The sample from the subject is typically a biological fluid as described above, and may be the same sample of biological fluid used to conduct the method described above. Numerous tests for CA-125 are known. See, e.g., R. Bast and R. Knapp, in Ovarian Malignancies: Diagnostic and Therapeutic Advances, at 11-25 (M. Piver ed. 1987).

Expression of Elafin also allows for the course of treatment of mullerian-derived tumors to be monitored. In this method, a biological sample is provided from a subject undergoing treatment, e.g., surgical, chemotherapeutic or hormonal treatment, for a mullerian-derived tumor. If desired, biological samples are obtained from the subject at various time points before, during, or after treatment. Expression of Elafin is then determined and compared to a reference, e.g. control whose mullerian derived tumor state is known. The reference sample has been exposed to the treatment. Alternatively, the reference sample has not been exposed to the treatment. Optionally, such monitoring is carried out preliminary at second look surgical surveillance procedures and subsequent surgical surveillance procedures. For example, samples may be collected from subjects who have received initial surgical treatment for ovarian cancer and subsequent treatment with antineoplastic agents for that cancer to monitor the progress of the treatment.

If the reference sample contains no mullerian-derived tumor cells, a similarity or a decrease in expression between Elafin in the test sample and the reference sample indicates that the treatment is efficacious. However, an increase in expression between Elafin in the test sample and the reference sample indicates a less favorable clinical outcome or prognosis.

By "efficacious" is meant that the treatment leads to a reduction in expression of a pathologically up-regulated gene, e.g., Elafin, CA-125, HE4 or SLPI or a decrease in size, prevalence, or metastatic potential of a mullerian derived tumor in a subject. Assessment of mullerian derived cancer is made using standard clinical protocols. Efficaciousness is determined in association with any known method for diagnosing or treating mullerian derived tumors.

Expression of Elafin or other cancer biomarkers (e.g., SLPI, HE4 or CA-125) is determined at the protein or nucleic acid level using any method known in the art. For example, Northern hybridization analysis using probes which specifically recognize one or more of these sequences can be used to determine gene expression. Alternatively, expression is measured using reverse-transcription-based PCR assays, e.g., using primers specific for the differentially expressed sequence of genes. Transcriptional profiling using cDNA microarray chips may also be used to measure expression of Elafin. Expression is also determined at the protein level, i.e., by measuring the levels of polypeptides encoded by the gene products described herein, or activities thereof. Such methods are well known in the art and include, e.g., immunoassays based on antibodies to proteins encoded by the genes. Any biological material can be used for the detection/quantification of the protein or its activity. Alternatively, a suitable method can be selected to determine the activity of proteins encoded by the marker genes according to the activity of each protein analyzed.

The difference in the level of Elafin in the control sample compared to the test sample is statistically significant. By statistically significant is meant that the alteration is greater than what might be expected to happen by chance alone.

Statistical significance is determined by method known in the art. For example statistical significance is determined by p-value. The p-values is a measure of probability that a difference between groups during an experiment happened by chance. ($P(z \geq z_{observed})$). For example, a p-value of 0.01 means that there is a 1 in 100 chance the result occurred by chance. The lower the p-value, the more likely it is that the difference between groups was caused by treatment. An alteration is statistically significant if the p-value is at least 0.05. Preferably, the p-value is 0.04, 0.03, 0.02, 0.01, 0.005, 0.001 or less.

The "diagnostic accuracy" of a test, assay, or method concerns the ability of the test, assay, or method to distinguish between patients having mullerian derived tumor or at risk for developing a mullerian derived tumor is based on whether the patients have a "clinically significant presence" of Elafin. By "clinically significant presence" is meant that the presence of the Elafin (e.g., mass, such as milligrams, nanograms, or mass per volume, such as milligrams per deciliter or copy number of an MTNA transcript per unit volume) in the patient (typically in a sample from the patient) is higher than the predetermined cut-off point (or threshold value) for that Elafin and therefore indicates that the patient has a mullerian derived tumor.

The terms "high degree of diagnostic accuracy" and "very high degree of diagnostic accuracy" refer to the test or assay for Elafin with the predetermined cut-off point correctly (accurately) indicating the presence or absence of the a mullerian derived tumor. A perfect test would have perfect accuracy. Thus, for individuals who have a mullerian derived tumor, the test would indicate only positive test results and would not report any of those individuals as being "negative" (there would be no "false negatives"). In other words, the "sensitivity" of the test (the true positive rate) would be 100%. On the other hand, for individuals who did not have a mullerian derived tumor, the test would indicate only negative test results and would not report any of those individuals as being "positive" (there would be no "false positives"). In other words, the "specificity" (the true negative rate) would be 100%. See, e.g., O'Marcaigh A S, Jacobson R M, "Estimating The Predictive Value Of A Diagnostic Test, How To Prevent Misleading Or Confusing Results," Clin. Ped. 1993, 32(8): 485-491, which discusses specificity, sensitivity, and positive and negative predictive values of a test, e.g., a clinical diagnostic test.

Changing the cut point or threshold value of a test (or assay) usually changes the sensitivity and specificity but in a qualitatively inverse relationship. For example, if the cut point is lowered, more individuals in the population tested will typically have test results over the cut point or threshold value. Because individuals who have test results above the cut point are reported as having the disease, condition, or syndrome for which the test is being run, lowering the cut point will cause more individuals to be reported as having positive results (i.e., that they have a mullerian derived tumor). Thus, a higher proportion of those who have a mullerian derived tumor will be indicated by the test to have it. Accordingly, the sensitivity (true positive rate) of the test will be increased. However, at the same time, there will be more false positives because more people who do not have the disease, condition, or syndrome (i.e., people who are truly "negative") will be indicated by the test to have Elafin values above the cut point and therefore to be reported as positive (i.e., to have the disease, condition, or syndrome) rather than being correctly indicated by the test to be negative. Accordingly, the specificity (true negative rate) of the test will be decreased. Similarly, raising the cut point will tend to decrease the sensitivity and increase the specificity. Therefore, in assessing the accuracy and usefulness of a proposed medical test, assay, or method for assessing a patient's condition, one should always take both sensitivity and specificity into account and be mindful of what the cut point is at which the sensitivity and specificity are being reported because sensitivity and specificity may vary significantly over the range of cut points.

There is, however, an indicator that allows representation of the sensitivity and specificity of a test, assay, or method over the entire range of cut points with just a single value. That indicator is derived from a Receiver Operating Characteristics ("ROC") curve for the test, assay, or method in question. See, e.g., Shultz, "Clinical Interpretation Of Laboratory Procedures," chapter 14 in Teitz, Fundamentals of Clinical Chemistry, Burtis and Ashwood (eds.), 4th edition 1996, W.B. Saunders Company, pages 192-199; and Zweig et al., "ROC Curve Analysis: An Example Showing The Relationships Among Serum Lipid And Apolipoprotein Concentrations In Identifying Patients With Coronary Artery Disease," Clin. Chem., 1992, 38(8): 1425-1428.

An ROC curve is an x-y plot of sensitivity on the y-axis, on a scale of zero to one (i.e., 100%), against a value equal to one minus specificity on the x-axis, on a scale of zero to one (i.e., 100%). In other words, it is a plot of the true positive rate against the false positive rate for that test, assay, or method. To construct the ROC curve for the test, assay, or method in question, patients are assessed using a perfectly accurate or "gold standard" method that is independent of the test, assay, or method in question to determine whether the patients are truly positive or negative for the disease, condition, or syndrome. The patients are also tested using the test, assay, or method in question, and for varying cut points, the patients are reported as being positive or negative according to the test, assay, or method. The sensitivity (true positive rate) and the value equal to one minus the specificity (which value equals the false positive rate) are determined for each cut point, and each pair of x-y values is plotted as a single point on the x-y diagram. The "curve" connecting those points is the ROC curve.

The area under the curve ("AUC") is the indicator that allows representation of the sensitivity and specificity of a test, assay, or method over the entire range of cut points with just a single value. The maximum AUC is one (a perfect test) and the minimum area is one half. The closer the AUC is to one, the better is the accuracy of the test.

By a "high degree of diagnostic accuracy" is meant a test or assay (such as the test of the invention for determining the clinically significant presence of Elafin, which thereby indicates the presence of a Mullerian derived tumor) in which the AUC (area under the ROC curve for the test or assay) is at least 0.70, desirably at least 0.75, more desirably at least 0.80, preferably at least 0.85, more preferably at least 0.90, and most preferably at least 0.95.

By a "very high degree of diagnostic accuracy" is meant a test or assay in which the AUC (area under the ROC curve for the test or assay) is at least 0.875, desirably at least 0.90, more desirably at least 0.925, preferably at least 0.95, more preferably at least 0.975, and most preferably at least 0.98.

The subject is preferably a mammal. The mammal is, e.g., a human, non-human primate, mouse, rat, dog, cat, horse, or cow. Subjects are typically human females. The methods are applicable to testing for mullerian-derived tumors such as ovarian cancer, e.g. epithelial ovarian cancer, endocervical cancer, fallopian cancer, or endometrial cancer. Ovarian cancer includes for example, serous tumors, mucinous tumors, endometrioid tumors, clear cell (mesonephroid) tumors, Brenner tumors (i.e., transitional), undifferentiated carcinoma, mixed epithelial tumors, and unclassified epithelial tumors. See, e.g., R. Scully, in Ovarian Malignancies: Diagnostic and Therapeutic Advances, at 28 (M. Piver, ed., 1987). Endometrial cancer includes any histological type, including (but not limited to) adenocarcinomas, adenoacanthomas, adenosquamous carcinomas, papillary serous carcinomas, and clear cell carcinomas.

The subject has been previously diagnosed as carrying mullerian-derived cancer, and possibly has already undergone treatment for the mullerian derived cancer. Alternatively, the subject has not been previously diagnosis as carrying mullerian derived cancer. The present invention is useful with all patients at risk for mullerian-derived cancer. Patients at risk for mullerian-derived cancer, for whom screening with the method of the present invention is particularly justified, include postmenopausal women on exogenous estrogen treatment, obese postmenopausal women (particularly if there is a family history of endometrial, breast, or ovarian cancer), women whose menopause occurred after 52 years of age, and premenopausal women with anovulatory cycles, such as those with polycystic ovarian disease. J. Berek and N. Hacker, supra at 286. Optionally, the subject is tested for carrying other indicators of susceptibility of developing cancer. For example, the subject is positive for BRCA1 or BRCA2.

Diagnosis of ovarian cancer is typically made through the identification of a mass on a pelvic examination, though it may also be through other means such as a radiological diagnosis, pelvic ultrasound, endocervical and cervical cytology, or the detection of a humoral marker such as CA-125. Treatment is typically through cytoreductive surgery, followed by treatment with antineoplastic agents (e.g., a combination of cisplatin or carboplatin with an alkylating agent such as cyclophosphamide). Diagnosis of endometrial carcinoma is typically through an endocervical curretage and endometrial biopsy, as no specific humoral marker is currently available. The treatment for endometrial carcinoma is generally total abdominal hysterectomy and bilateral salpingoophrectomy. In addition, many patients will require subsequent radiation therapy.

Immunotherapy is one of many ways in which Elafin, and the other cancer markers of the invention, are used in therapeutic intervention in cancer disease. Immunotherapeutics, generally, rely on the use of immune effector cells and molecules to target and destroy cancer cells. The immune effector is, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

It is desirable to confirm that cancer patients have CTLs that are reactive against the cancer markers of the invention, such as Elafin, when the antigens are presented on autologous cancer cells.

Cancer patients are treated by the administration of an effective amount of one or more antibodies that specifically bind to one or more of the proteins or peptides encoded by the cancer markers of the present invention, e.g., administration of anti-Elafin antibodies. This types of therapy is akin to "passive immunity". A number of different approaches for passive immunotherapy of cancer exist. They may be broadly categorized into the following: injection of antibodies alone; injection of antibodies coupled to toxins or chemotherapeutic agents; injection of antibodies coupled to radioactive isotopes; injection of anti-idiotype antibodies; and finally, purging of tumor cells in bone marrow. All such techniques are used in this invention. Humanized or human monoclonal antibodies can also be employed in passive immunotherapy.

Alternatively, cancer patients are treated by the administration of an effective amount of one or more cancer marker antigens, such as Elafin. These therapies are linked to "active immunity". In active immunotherapy, purified antigens, recombinant cells expressing such antigens, and irradiated autologous or allogeneic tumor cell compositions expressing such antigens may be used. Administration may be combined with general adjuvants, such as BCG.

An effective T cell response can also be mounted without MHC expression, e.g., in MHC class II negative lymphoma. NK cells also target cells that lack MHC. Recombinant Elafin protein or a chimeric Elafin-helper molecule plus adjuvant is used to activate an anti-Elafin response. Given that Elafin is not expressed in most normal tissues, the possibility of side toxicity or autoimmunity is contemplated to be minimal during such immunotherapy.

Autologous cells, such as macrophages and dendritic cells, may be pulsed with a cancer marker peptide of the invention, such as Elafin or peptide thereof, and then administered to a cancer patient. Similarly, autologous cells may be adapted to recombinantly express a cancer marker peptide, such as Elafin, before re-administration to a patient. Any recombinant expression vector may be used, such as a viral vector.

Immunoassays carried out in accordance with the present invention may be homogeneous assays or heterogeneous assays. In a homogeneous assay the immunological reaction usually involves the specific antibody (e.g., Elafin, HE4, CA-125, or SLPI), a labeled analyte, and the sample of interest. The signal arising from the label is modified, directly or indirectly, upon the binding of the antibody to the labeled analyte. Both the immunological reaction and detection of the extent thereof are carried out in a homogeneous solution. Immunochemical labels which may be employed include free radicals, radioisotopes, fluorescent dyes, enzymes, bacteriophages, or coenzymes.

In a heterogeneous assay approach, the reagents are usually the sample, the antibody, and means for producing a detectable signal. Samples as described above may be used. The antibody is generally immobilized on a support, such as a bead, plate or slide, and contacted with the specimen suspected of containing the antigen in a liquid phase. The support is then separated from the liquid phase and either the support phase or the liquid phase is examined for a detectable signal employing means for producing such signal. The signal is related to the presence of the analyte in the sample. Means for producing a detectable signal include the use of radioactive labels, fluorescent labels, or enzyme labels. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays are radioimmunoassays, immunofluorescence methods, or enzyme-linked immunoassays.

Those skilled in the art will be familiar with numerous specific immunoassay formats and variations thereof which may be useful for carrying out the method disclosed herein. See generally E. Maggio, Enzyme-Immunoassay, (1980) (CRC Press, Inc., Boca Raton, Fla.); see also U.S. Pat. No. 4,727,022 to Skold et al. titled "Methods for Modulating Ligand-Receptor Interactions and their Application," U.S. Pat. No. 4,659,678 to Forrest et al. titled "Immunoassay of Antigens," U.S. Pat. No. 4,376,110 to David et al., titled "Immunometric Assays Using Monoclonal Antibodies," U.S. Pat. No. 4,275,149 to Litman et al., titled "Macromolecular Environment Control in Specific Receptor Assays," U.S. Pat. No. 4,233,402 to Maggio et al., titled "Reagents and Method Employing Channeling," and U.S. Pat. No. 4,230,767 to Boguslaski et al., titled "Heterogenous Specific Binding Assay Employing a Coenzyme as Label."

Antibodies are conjugated to a solid support suitable for a diagnostic assay (e.g., beads, plates, slides or wells formed from materials such as latex or polystyrene) in accordance with known techniques, such as precipitation. An antibody or antibody fragment which binds to CA-125 or CEA may optionally be conjugated to the same support, as discussed above. Antibodies as described herein may likewise be conjugated to detectable groups such as radiolabels (e.g., 35 S, 125 I, 131 I), enzyme labels (e.g., horseradish peroxidase, alkaline phosphatase), and fluorescent labels (e.g., fluorescein) in accordance with known techniques.

Diagnostic kits for carrying out the methods described herein are produced in a number of ways. In one embodiment, the diagnostic kit comprises (a) an antibody (e.g., Elafin) conjugated to a solid support and (b) a second antibody of the invention conjugated to a detectable group. The reagents may also include ancillary agents such as buffering agents and protein stabilizing agents, e.g., polysaccharides and the like. The diagnostic kit may further include, where necessary, other members of the signal-producing system of which system the detectable group is a member (e.g., enzyme substrates), agents for reducing background interference in a test, control reagents, apparatus for conducting a test, and the like. Alternatively, a test kit contains (a) an antibody, and (b) a specific binding partner for the antibody conjugated to a detectable group. Ancillary agents as described above may likewise be included. The test kit may be packaged in any suitable manner, typically with all elements in a single container along with a sheet of printed instructions for carrying out the test.

EXAMPLE 1

General Methods

Cell Lines

Fourteen established ovarian carcinoma cell lines were used to evaluate the mRNA and protein expression levels of HE4, Elafin and SLPI. They included OVCAR-5, OVCAR-8, IGROV-1, OVCA420, OVCA429 MCAS, TOV-112D, CaoV3, OVCAR-3, SKOV-3, OV-90, ES-2, and TOV-21 G. The SNU-251 endometrioid ovarian cancer cell line, which harbors a BRCA1 mutation, was purchased from the Korean Cell Line Bank, Seoul National University, Seoul, Korea. All ovarian cancer cell lines, except SNU-251 and ES-2, were propagated in 1:1 MCDB105 and Media 199 (Sigma-Aldrich, St. Louis, Mo.) supplemented with 15% fetal bovine serum and 1% penicillin/streptomycin (Life Technologies, Inc., Gaithersburg, Md.) at 37° C. in a 10% CO2-containing atmosphere. The ES-2 clear cell carcinoma line was propagated in McCoy's 5A modified medium with 10% fetal bovine serum. The SNU-251 line was propagated in RPMI 1640 supplemented with 10% fetal bovine serum. In addition, HeLa and IMR90 cells were obtained from the American Type Culture Collection and propagated in DMEM with 10% fetal bovine serum. HE4 expression in these cancer cell lines was compared with that of primary human ovarian surface epithelial cells (HOSE) and to human telomerase-immortalized OSE (IOSE).

RNA Extraction and RT-PCR. Cells were grown to 80% to 90% confluence. Medium was carefully aspirated from cell cultures and cells were lysed in 1 mL/dish of Trizol reagent (Life Technologies). Total RNA was extracted according to the manufacturer's recommendation. RNA was quantitated using a spectrophotometer. cDNA was synthesized from each cell line using 2 ug of total RNA. Oligo(dT) primers were used for the first-strand synthesis as described in the SuperScript First-Strand Synthesis System for RT-PCR (Invitrogen, Carlsbad, Calif.). PCR primers for HE4 were designed using Primer3 (http://frodo.wi.mit.edu/cgi-bin/primer3/primer3_www.cgi). The primer pairs for HE4 were (forward) 5'-CGGCTTCACC C-TAGTCTCAG-3' (SEQ ID NO:3), (reverse) 5'-CCTCCTTATCATTGGGCAGA-3' (SEQ ID NO:4) and those for h-actin were (forward) 5'-ACAGAGCCTCGC-CTTTGC-3'(SEQ ID NO:5), (reverse) 5'-AGGATGC-CTCTCTTGCTCTG-3'(SEQ ID NO: 6). PCR primers for Eppin-1 were previously described. Testes cDNA was obtained from BD Biosciences, Clontech (Palo Alto, Calif.). PCR products were resolved and visualized on a 2% TAE agarose/ethidium bromide gel. The identity of the HE4 PCR product was confirmed by DNA sequencing. Recombinant HE4 Proteins. To generate a baculovirus gene construct, the HE4 complementary DNA without its intrinsic signal peptide-coding sequence was modified for insertion into the pMel-BacB transfer vector (Invitrogen) by PCR with oligonucleotides that incorporated BamHI and HindIII enzyme restriction sites into the ends. Inserts were ligated into the pMelBacB-vector after restriction digest, transformed, and amplified in *Escherichia coli* Top10. Insert-containing clones were selected and confirmed by dideoxynucleotide sequencing on both strands. After cotransfection of the transfer vector with a linearized defective baculovirus DNA (Bac-N-Blue linear DNA, Invitrogen) into Sf9 insect cells, viable recombinant baculoviral clones were selected from plaque assay. Pure recombinant baculovirions were propagated to obtain high titer viral stock and used to infect High Five insect cells at a multiplicity of three plaqueforming units per cell. HE4 Antibodies. The NH2 terminus of HE4 contains a signal peptide with a predicted cleavage site for a signal peptidase between codons 30 and 31. HE4-specific antibodies were produced by immunizing rabbits with a glutathione S-transferase (GST) fusion protein composed of the mature form of HE4 (amino acids 31-125) and GST. New Zealand White rabbits were immunized eight times against the glutathione S-transferase fusion protein. Serum was harvested after the rabbits showed significant anti-GST-HE4 and anti-rHE4 titer. Affinity purified antibodies were generated by adsorption of the crude antisera to a GST affinity column (Pierce Biotechnology, Inc., Rockford, Ill.) to remove all the GST antibodies. The GST antibody-depleted serum was then affinity-purified by passing it over a GST-HE4 column generated using an AminoLink Coupling Gel column (Pierce Biotechnology). The antibodies were eluted with 100 mmol/L glycine (pH 2.8), neutralized, and finally dialyzed against PBS (pH 7.4) with 50% glycerol. The final concentration of the affinity-purified HE4 antibody was 205 ng/L. The GST antibodies were eluted and dialyzed in a similar fashion and served as a negative control.

Tissue Specimens

Following institutional review board approval, the records of the Division of Women's and Perinatal Pathology in the Department of Pathology at Brigham and Women's Hospital (Boston, Mass.) were reviewed for ovarian carcinomas from 2001 to 2004. Inclusion criteria included (a) primary ovarian carcinoma, including the four major histopathologic subtypes (serous, endometrioid, clear cell, and mucinous) and (b) ovarian carcinoma with residual histologically identified normal ovary. Exclusion criteria were (a) metastatic carcinoma to the ovary and (b) tumors of low malignant potential (borderline tumors). All in all, 92 cases were identified. All the tumors were stages III and IV; all the serous tumors and the majority of endometrioid tumors were of high grade, thus correlation of staining with grade and stage could not be evaluated. Each case was reviewed and appropriate blocks designated for immunohistochemistry. In addition, 11 cases were identified in which normal ovaries were removed incidentally for another procedure unrelated to malignancy. These were used to evaluate the expression pattern in normal ovarian tissues. To further study the protein expression in these and other normal human tissues, five to six samples of formalin fixed tissue from different patients for several tissues, including brain, esophagus, stomach, duodenum, gallbladder, pancreas, colon, liver, kidney, spleen, lymph node, thyroid, lung, trachea, heart, prostate, testes, breast, fallopian tubes, endometrium, cervix, testis, and epididymis. To examine expression in other nonovarian carcinomas, paraffin embedded in-house whole sections were used and a multiple tumor tissue microarray provided by the Dana-Farber Harvard Cancer Center Core Facilities.

Immunohistochemistry

Immunohistochemical localization of protein was done on 4-Am sections from formalin-fixed, paraffin-embedded tissue. Affinity-purified rabbit polyclonal antibody was used at a dilution of 1:10,000 with heat-induced epitope retrieval. This antibody was detected using the Envision+system (K4011, DakoCytomation, Carpinteria, Calif.) that employs horseradish peroxidase-labeled polymer conjugated to goat anti-rabbit immunoglobulin antibodies. The immune complexes were identified using a peroxidase reaction with 3,3'-diaminobenzidine plus as chromogen. The positive control for HE4 staining was human epididymis. Polyclonal nonimmune rabbit IgG antibodies and anti-GST antibodies, generated as a byproduct of the HE4 antibody purification, were used as negative controls to show the specificity of the HE4 affinity-purified antibodies. Slides were counterstained with Mayer's hematoxylin. Antibodies against SLPI were purchased from R&D Systems (Minneapolis, Minn.).

Immunofluorescence

SKOV-3, CaoV3, and OVCAR-5 cells were grown on coverslips, fixed with 70% methanol, and permeabilized with 0.5% Triton X-100 as previously described (31). Cells were double labeled by incubation with the rabbit polyclonal antibodies to HE4 (1:5,000), and monoclonal antibodies against the 58K Golgi protein formiminotransferase cyclodeaminase (1:150; Abcam, Inc., Cambridge, Mass.), or KDEL monoclonal antibodies against the endoplasmic reticulum protein Grp78 (1:300; EMD Biosciences, Inc., San Diego, Calif.) in PBS with 5% goat serum. After washing, appropriate species-specific, fluorochrome-conjugated secondary antibodies (Jackson ImmunoResearch Laboratories, West Grove, Pa.) were applied as recommended by the manufacturer, and fluorescence was visualized with a Zeiss Axioskop 2 microscope using AxioVision Software for Digital Microscopy.

Glycosylation Analysis

CaoV3 and OVCAR-5 cells were grown in 1:1 MCDB105 and Media 199 (Sigma-Aldrich) supplemented with 15% fetal bovine serum and 1% penicillin/streptomycin (Life Technologies) to 90% confluence. The medium was then changed to 1:1 MCDB105 and Media 199 without any fetal bovine serum and the cells were cultured for an additional 48 hours. The cultured medium was then cleared by centrifugation and concentrated using a Millipore Amicon Ultra-15 centrifugal filter with a 5,000 molecular weight cutoff. Twenty micrograms of the concentrated cultured medium were then denatured in denaturing buffer (5% SDS, 10% β-mercaptoethanol) at 100° C. for 10 minutes. One-tenth volume of both G7 buffer (0.5 mol/L sodium phosphate (pH 7.5) at 25° C.] and 10% NP40 surfactant were then added, followed by 2 uL of N-Glycosidase F (PNGase F; New England BioLabs, Beverly, Mass.). The reaction was then incubated at 37° C. for 1 hour. Reaction products were denatured and resolved on a 4% to 12% SDS-polyacrylamide gel and analyzed by Western blot using the affinity-purified HE4 antibody (1:4,000).

Statistical Analysis

Comparison of papillary serous immunostaining with endometrioid, mucinous, and clear cell subtypes was accomplished by using exact version of Kruskal-Wallis nonparametric test for singly ordered R×C contingency tables (Software: StatXact, version 6.1 2003, from Cytel Software, Cambridge, Mass.).

EXAMPLE 2

Evaluation of Expression of HE4 Protein in Normal Human Tissues

Figure 1B:
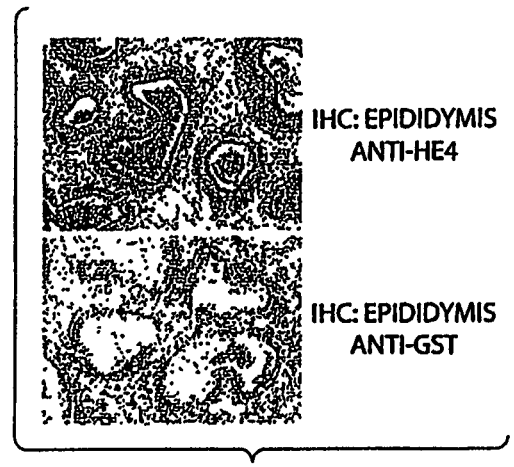
FIG. 1B is a photograph of immunohistochemical (IHC) staining of human epididymis with HE4 antibodies (20× objective) showing an apical and luminal distribution. GST antibodies at higher concentrations than those used for HE4 did not elicit a specific signal in the epididymis.
Figure 1C:
FIG. 1C is a photograph of a Western Blot showing that HE4 antibodies can detect GST-HE4 and recombinant HE4 synthesized in High Five insect cells.
Figure 1D:
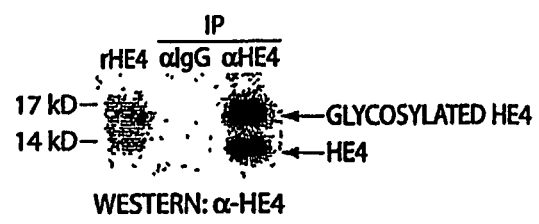
FIG. 1D is a photograph of a Western Blot showing that HE4 antibodies can specifically immunoprecipitate recombinant HE4, including the glycosylated form. Preimmune normal rabbit IgG served as a negative control.

HE4 was first described as an epididymis-specific gene using Northern blot analysis and in situ transcript hybridization. To characterize the distribution of HE4 protein in benign and malignant tissues affinity purified HE4 antibodies were raised and assessed their immunohistochemical profile in human epididymis. The HE4 antibodies localized to the duct of the epididymis in a granular apical pattern, consistent with prior studies using in situ transcript hybridization (FIG. 1B). No HE4 protein was detected in the surrounding stroma or vasculature. Importantly, affinity-purified antibodies against GST, a byproduct of the HE4 antibody purification, and purified nonimmune IgG failed to produce a signal in this tissue under similar conditions (FIG. 1B and data not shown). In addition, the HE4 antibodies could detect the immunizing antigen (GST-HE4) and a recombinant form of HE4 generated by baculovirus infection of High Five insect cells by Western blot analysis (FIG. 1C). Finally, these antibodies could specifically immunoprecipitate the insect cell-derived recombinant HE4, including the glycosylated 17-kDa form (for example, see FIG. 4D), whereas the preimmune immunoglobulins could not (FIG. 1D). A collection of formalin-fixed, paraffin-embedded normal human tissues to study the presence and distribution of HE4 in these tissues was assembled. Under conditions where the HE4 antibody shows specific immunostaining for HE4 in the epididymis, it was found that the expression of the HE4 protein is highly restricted in normal human tissues (Table 2). Specifically, HE4 was expressed most highly in the epididymis and in the female reproductive tract (fallopian tubes, endometrium, and endocervix). HE4 expression was also present in the respiratory epithelium, especially in the trachea. Occasional staining was also observed in the epithelium of the renal convoluted tubules and salivary gland ducts. HE4 protein was notably absent from the GI tract, liver, pancreas, spleen, lymph nodes, mesenchymal tissues (heart, skeletal muscle), breast, and brain. There was nonspecific staining of colloid in the thyroid but the epithelium was negative. Under similar conditions, antibodies against another WAP domain containing protein, SLPI (FIG. 1A), show widespread expression in multiple epithelia in the body. (Table 3) Therefore, expression of HE4 protein is highly restricted in normal tissues and tends to consistently identify epithelia in the reproductive tracts and central respiratory airways.

TABLE 2

HE4 protein expression in normal human tissues

| Normal tissues | Positive/tested | Histological description |
|---|---|---|
| Esophagus | 0/2 | |
| Stomach | 0/4 | |
| Gallbladder | 0/5 | |
| Duodenum | 0/6 | |
| Colon | 0/6 | |
| Pancreas | 0/4 | |
| Liver | 0/5 | |
| Spleen | 0/5 | |
| Lymph node | 0/7 | |
| Skeletal muscle | 0/4 | |
| Cardiac muscle | 0/4 | |
| Lung | 1/4 | Proximal respiratory epithelium |
| Trachea | 5/5 | Respiratory epithelium and minor salivary glands |
| Thyroid | 0/6 | |
| Kidney | 5/6 | Focal in a minority of tubules |
| Brain | 0/4 | |
| Breast | 4/5 | Predominantly in secretions with focal reactivity in a minority of ducts |
| Ovary | 0/7 | Negative in OSE; positive in metaplastic, ciliated CICs |
| Fallopian tubes | 10/10 | |
| Endometrium | 4/4 | |
| Cervix | 4/4 | Endocervical glands only |
| Epididymis | 5/5 | Strongest staining in duct of the epididymis, weaker staining in efferent ducts |
| Testes | 0/4 | |
| Prostate | 4/7 | Weak, focal glandular epithelial staining |

TABLE 3

Immunohistochemical staining of normal human tissues with SLPI[#] antibodies[*]

| Normal tissues | Positive/Tested | Histological description |
|---|---|---|
| Esophagus | 2/2 | Basal epithelium, cytoplasmic stain |
| Stomach | 4/4 | Glands |
| Gallbladder | 5/5 | |
| Duodenum | 6/6 | |
| Colon | 6/6 | |
| Pancreas | 4/4 | Acini and ducts |
| Liver | 5/5 | Hepatocytes and bile ducts (cytoplasm only) |
| Spleen | 0/4 | |
| Lymph node | 0/7 | |
| Skeletal muscle | 0/4 | |
| Cardiac muscle | 0/4 | |
| Lung | 4/4 | Bronchial epithelium |
| Thyroid | 6/6 | |
| Kidney | 6/6 | Tubules |
| Brain | 0/4 | |
| Breast | 4/5 | |
| Ovary | 7/7 | Positive in OSE, CICs, and granulosa cells |
| Fallopian tubes | 10/10 | |
| Endometrium | 4/4 | |
| Cervix | 4/4 | Endocervical glands |
| Epididymis | 5/5 | Efferent and main duct of epididymis |
| Testes | 1/4 | Weak, diffuse |
| Prostate | 6/6 | |

[#]SLPI = secretory leukocyte protease inhibitor
[*]SLPI antibody purchased from R&D Systems, catalog #: AB-260-NA

EXAMPLE 3

Figure 2A:
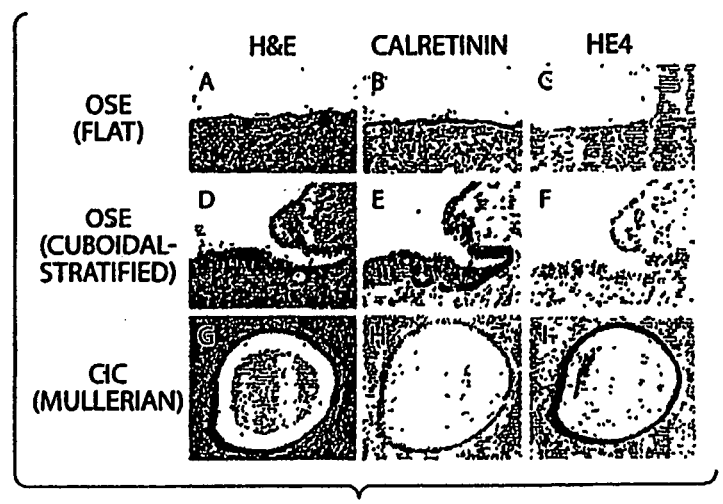
FIG. 2A is a photograph showing examples of OSE and CICs stained with H&E, the normal OSE marker calretinin, and HE4. HE4 expression is absent in flat (C) or cuboidal (F) OSE but is abundantly present in the epithelium lining metaplastic CICs (I). Calretinin expression (middle) is limited to the OSE. (A-C, 20× objective; D-F, 40× objective; G-I, 20× objective).
Figure 2B:
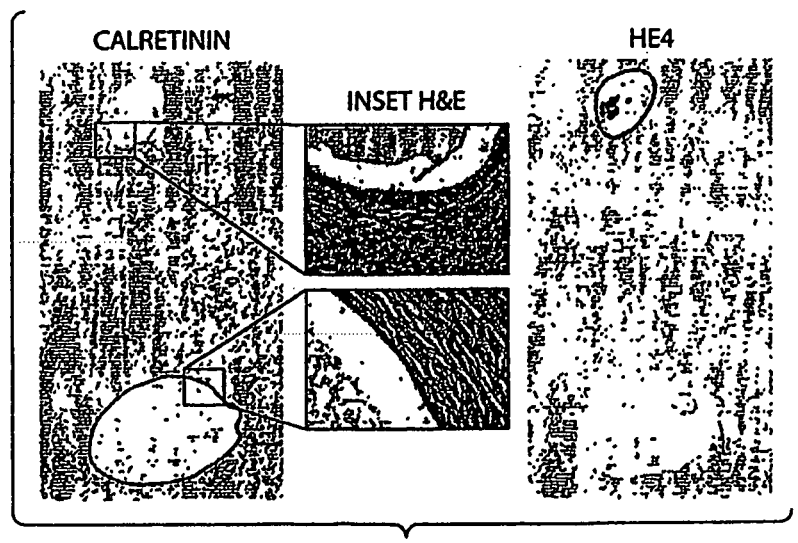
FIG. 2B is a photograph of HE4 and calretinin showing differential expression in cortical inclusion cysts. A section of normal ovary containing two different CICs was identified and stained with antibodies against calretinin and HE4 (10× objective). Histologic examination (H&E insets, 40× objective) showed the top CIC lined by Mullerian type epithelium and the bottom CIC lined by flat mesothelium. HE4 expression is limited entirely to the CIC with Mullerian epithelium.

HE4 Protein is Expressed in the Mullerian Epithelium of Cortical Inclusion Cysts in Normal Ovaries It had previously been reported that Mullerian metaplasia of the OSE, frequently seen in cortical inclusion cysts (CIC), heralds the expression of a number of ovarian cancer biomarkers, including EpCAM, Mucin 1, Mesothelin, and CD9. To address whether HE4 is expressed by surface epithelial cells and/or by the Mullerian epithelia in CICs, 11 ovaries were stained that were histologically proven benign. The calcium binding protein calretinin was used as a positive control for the OSE, because it has been previously showed that calretinin stains normal OSE but not metaplastic or neoplastic ovarian epithelium. Neither the flat nor the more cuboidal and stratified OSE expressed any HE4 protein under conditions where calretinin could easily be detected (FIG. 2A). Conversely, in cortical inclusion cysts with Mullerian epithelium, HE4 was readily detected whereas calretinin was negative in such CICs (FIG. 2A). However, in CICs that still maintained the flat morphology of the OSE the opposite was true; HE4 was negative and calretinin was positive (FIG. 2B). Therefore, expression of HE4 protein, like certain other ovarian biomarkers identified by gene expression profiling, is acquired during the normal, age-related process of CIC formation and Mullerian metaplasia.

EXAMPLE 4

HE4 is Overexpressed in Serous and Endometrioid Ovarian Carcinomas

Figure 3:
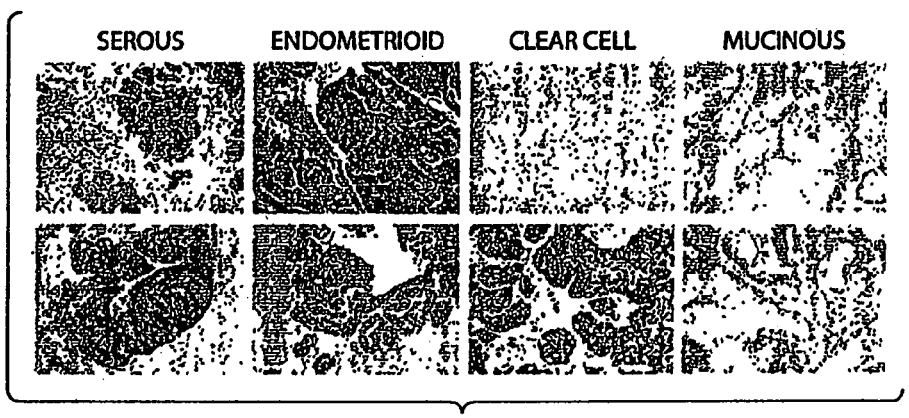
FIG. 3 is a series of photographs showing that HE4 is expressed by subtypes of ovarian carcinomas. There are two examples each of HE4 expression in serous, endometrioid, clear cell, and mucinous carcinomas. HE4 is common in serous and endometrioid subtypes and tends to be diffusely distributed in these tumors. Expression in clear cell carcinomas is less common and completely absent in mucinous carcinomas. Surrounding stroma and inflammatory cells are negative.

To address whether HE4 protein is overexpressed by ovarian carcinomas, 92 unique ovarian carcinoma tissue blocks were obtained with institutional review board approval from the Women's and Perinatal Division of Pathology in the Department of Pathology at Brigham and Women's Hospital. These samples were from women treated at the Dana-Farber/Brigham and Women's Cancer Center between 2001 and 2004. The cases included 60 serous carcinomas, 16 endometrioid carcinomas, 10 mucinous carcinomas, and 6 clear cell carcinomas. Human epididymis served as a positive control and all cases were selected to include some residual nontumor stromal, adipose, and/or vascular tissue as a negative control for HE4 staining. HE4 immunoreactivity was readily detected in the serous and endometrioid tumors as perinuclear, cytoplasmic, and membranous staining (FIG. 3). Of the serous carcinomas, 93% exhibited moderate-to-strong staining and the vast majority (90-100%) of these cases showed diffuse immunoreactivity throughout the tumor epithelia. Every endometrioid carcinoma was diffusely immunoreactive with HE4 antibodies. Of the 10 mucinous carcinomas, nine were completely negative for HE4 (FIG. 3; Table 4). These differences were statistically significant. The one case of mucinous carcinoma that was positive was a high-grade carcinoma in which both epithelial and stromal components showed immunoreactivity. We have not detected stromal HE4 immunostaining in any other case, nor do we see HE4 RNA expressed by normal human diploid fibroblasts (IMR90 cells; see below). HE4 immunoreactivity in clear cell carcinomas was intermediate, with three of six cases exhibiting moderate-to-strong staining (FIG. 3, Table 4). The distribution of staining in these tumors was heterogenous (50-100% of cells). We then asked whether the overexpression of HE4 was unique to ovarian carcinomas or is distributed across a spectrum of otherwise disparate epithelial tumors. A combination of multitumor tissue microarrays and in-house surgical specimens were used. Surprisingly, the majority of common nonovarian carcinomas did not exhibit HE4 immunostaining, including colon, breast, non-small cell lung, bladder, kidney, thyroid, and prostate cancers (Table 5). The exception was endometrial carcinoma, a finding that is not surprising given the Mullerian origins of this carcinoma.

TABLE 4

Summary of immunohistochemical staining of ovarian carcinomas with HE4 antibodies
Intensity of immunostaining*

| Histologicsubtytpes | Strong(% diffusec) | Moderate(% diffuse) | Weak(% diffuse) | Negative | Pb |
|---|---|---|---|---|---|
| Papillaryserous(n = 60) | 24(100) | 32(90) | 4(75) | 0 | |
| Endometrioid(n = 16) | 12(100) | 4(100) | 0 | 0 | 0.014 |
| Mucinous(n = 10) | 0 | 1x | 0 | 9 | 0.001 |
| Clearcell(n = 6) | 2(100) | 1(50) | 0 | 3 | 0.10 |

TABLE 5

Immunostaining of HE4 in non-ovarian carcinomas

| Tumor | Positive/Tested |
|---|---|
| Breast | 1/4 |
| Colon | 0/10 |
| Endometrium | 3/4 |
| Lung (NSCLC) | 1/4 |
| Thyroid | 0/4 |
| Prostate | 0/4 |
| Bladder | 0/3 |
| Kidney | 0/ |

EXAMPLE 5

HE4 is Expressed and Secreted as a Glycoprotein by Ovarian Carcinoma Cells

Figure 4A:
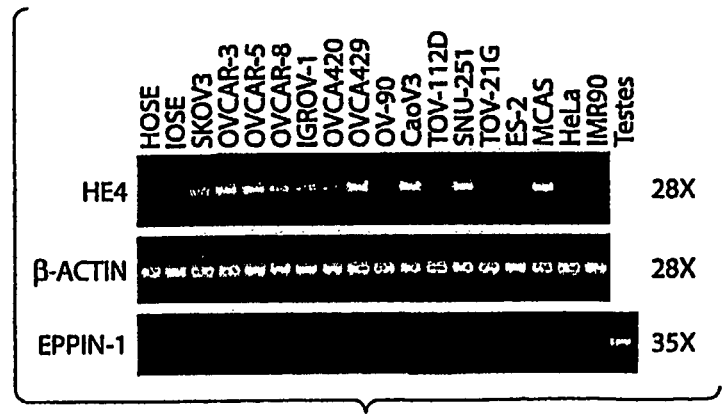
FIG. 4A is a photograph of semiquantitative RT-PCR analysis showing that HE4 is over expressed and secreted as a glycoprotein by ovarian carcinoma cells. Normal OSE (HOSE) and IOSE RNA served as negative controls for HE4 expression. Expression of actin served as a loading control.

HE4 expression in the epididymis was reported to be apical/membranous and within the duct lumen where it is in contact with spermatozoa. This pattern of expression is consistent with the fact that the cDNA for HE4 predicts a small, secretory protein with hydrophobic amino acids at the NH2 terminus consistent with a signal peptide. Cleavage of the signal peptide is predicted to yield a mature secretory polypeptide with a consensus site for N-glycosylation at amino acid position 15 (N-C-T). Based upon the observation that HE4 protein is overexpressed in human ovarian carcinomas it was necessary determined whether HE4 is also secreted by ovarian cancer cells, as is seen in the epididymis. To address this possibility, a collection of 14 established ovarian carcinoma cell lines was assembled and semiquantitative RT-PCR was used to identify those lines that endogenously overexpress HE4 relative to normal primary HOSE and IOSE. Consistent with the immunohistochemical data (FIG. 2), HE4 RNA was not detected in HOSE or IOSE (FIG. 4A). HE4 RNA was also not detected in HeLa or IMR90 cells. Conversely, the majority of the ovarian carcinoma lines expressed varying degrees of HE4 RNA. Equal loading was confirmed by RT-PCR for β-actin.

Figure 4B:
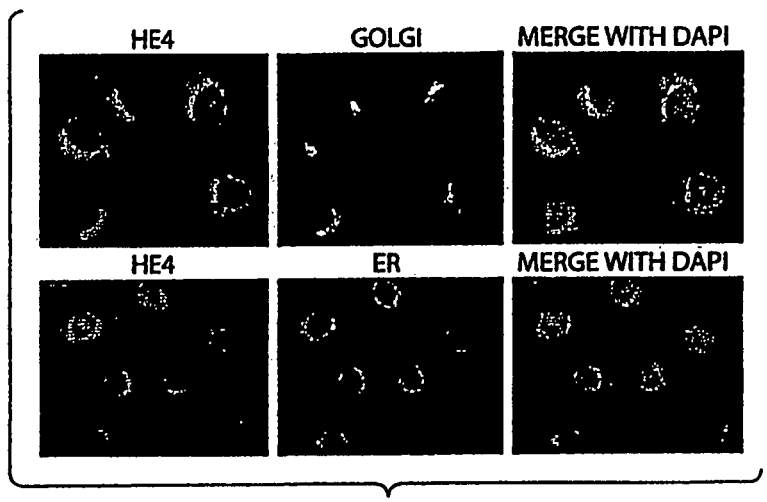
FIG. 4B is a series of photographs showing that HE4 is localized to the perinuclear Golgi apparatus and endoplasmic reticulum (ER). Immunofluorescence localization of HE4 in SKOV-3 cells revealed a perinuclear pattern that partially colocalized with the 58K Golgi protein and Grp78, an ER marker. Images were merged with 4V,6-diamidino-2-phenylindole (DAPI) to show the nucleus. Similar results were obtained in CaoV3 and OVCAR-5 cells.
Figure 4C:
FIG. 4C is a photograph of a Western Blot showing that HE4 is secreted by ovarian cancer cells. Conditioned medium from IOSE, CaoV3, OVCAR-5, TOV-21G, and ES-2 cells was concentrated and analyzed by Western blot for HE4. Secreted HE4 migrates as a higher molecular weight species compared with recombinant HE4.
Figure 4D:
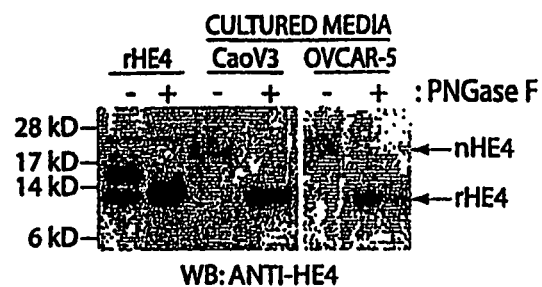
FIG. 4D is a photograph of a Western blot showing that secreted HE4 is N-glycosylated. Cultured medium was incubated with PNGase F, a deglycosylation enzyme.

To determine the intracellular localization of HE4 in ovarian cancer cells, SKOV-3, OVCAR-5, and CaoV3 cells were subjected to indirect immunofluorescence using the HE4 polyclonal antibodies. HE4 antibodies localized into perinuclear structures (FIG. 4B, bottom) and in some cells into dome-shaped perinuclear structures with a polarity that resembled the Golgi apparatus (FIG. 4B, top). Indeed, double staining with antibodies against 58K formiminotransferase cyclodeaminase, a known resident enzyme of the Golgi complex, showed partial colocalization with HE4 (FIG. 4B). Antibodies against Grp78, a component of the endoplasmic reticulum also showed partial colocalization with HE4, a finding consistent with proteins that are processed through the endoplasmic reticulum and Golgi for extracellular transport. To determine whether ovarian cancer cells can secrete HE4 cells were cultivated that express HE4 RNA (OVCAR-5 and CaoV3) and those that only express minute amounts or none at all (IOSE, TOV-21G, and ES-2). The cells were grown to 80% confluence, the medium was replaced with medium lacking serum and the cells were incubated for an additional 48 hours. The conditioned medium was then harvested, concentrated, and analyzed by Western blot for the presence of secreted HE4. Both CaoV3 and OVCAR-5 secreted a modified form of HE4 that migrated larger than the recombinant HE4 produced in insect cells (FIG. 4C). Secreted HE4 from HOSE, IOSE, or the two cancer lines that lacked significant HE4 expression by RT-PCR could not be detected. Because HE4 is predicted to undergo glycosylation, it was determined whether the altered migration of HE4 in the cultured medium could be explained by such a post-translational modification. Indeed, treatment of the cultured medium with the deglycosylating enzyme N-glycosidase F (PNGase F) dramatically altered the migration of the secreted HE4, resulting in a form that comigrates with recombinant HE4 (FIG. 4D). Therefore, these results show that ovarian carcinoma cells express HE4 and that the resulting gene product is N-glycosylated and secreted into the extracellular environment. Interestingly, the pattern of HE4 glycosylation in human cancer cells was different that the one seen in the High Five embryonic ovarian insect cells. Glycosylated HE4 in OVCAR-5 and CaoV3 migrated with an approximate molecular weight of 25 kDa whereas the glycosylated form of HE4 in the insect cells migrated as a 16-kDa species (FIG. 4D).

Moreover, the specificity of HE4 expression was challenged by asking whether Eppin-1, another WAP domain containing protein encoded on chromosome 20 next to HE4 (FIG. 1A), is also expressed in ovarian carcinomas. Eppin-1 RNA was not detected in the ovarian cancer cells lines, although Eppin-1 was clearly expressed in the testes, as previously reported (FIG. 4A; ref. 30).

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for facilitating the diagnosis of a cancer of mullerian origin in a subject, comprising
    detecting a presence or an absence of an Elafin polypeptide in a sample from said subject; and
    correlating the presence of said Elafin polypeptide with the presence of a cancer of mullerian origin in said subject;
wherein the diagnosis of a cancer of mullerian origin in said subject is facilitated.

2. The method of claim 1, wherein said cancer is ovarian cancer, endocervical cancer, fallopian cancer, or uterine cancer.

3. The method of claim 2, wherein said ovarian cancer is serous type, endometriod type, mucinous type, clear cell type, or transitional type.

4. The method of claim 1, wherein said subject has previously been treated surgically or hormonally for said cancer.

5. The method of claim 1, wherein said subject is BRAC1 or BRAC2 positive.

6. The method of claim 1, wherein the Elafin polypeptide has a molecular weight of approximately 12.3 kDa.

7. The method of claim 1, wherein the Elafin polypeptide has a molecular weight of approximately 9.9 kDa.

8. The method of claim 1, wherein the Elafin polypeptide has a molecular weight of approximately 6.0 kDa.

9. A method according to claim 1, wherein said sample is serum, blood plasma, ascites fluid, urine, vaginal secretion, or tissue biopsy.

10. The method of claim 1, wherein the Elafin polypeptide is detected electrophoretically, or immunochemically.

11. The method of claim 10, wherein said immunochemical detection is by radio-immune assay, immunofluorescence assay or by an enzyme-linked immunosorbant assay.

12. A method according to claim 1, further comprising detecting the presence of HE4, SLPI or CA-125 in said subject.

13. A method according to claim 1, wherein said subject has not been previously diagnosed as having cancer.

14. A method according to claim 1, wherein said subject has been previously diagnosed as having cancer.

15. A method for monitoring the progression of a mullerian derived cancer in a patient, comprising
    a) detecting the presence of an Elafin polypeptide in a first sample from said patient at a first period of time,
    b) detecting the presence of the Elafin polypeptide in a second sample from said patient at a second period of time
    c) comparing the amount of polypeptide detected in step (a) to the amount detected in step (b),
    wherein the cancer is progressing if the amount of the polypeptide increases over time, whereas the cancer is not progressing if the amount of the polypeptide remains constant or decreases over time.

16. The method of claim 15, wherein said cancer is ovarian cancer, endocervical cancer, fallopian cancer, or uterine cancer.

17. The method of claim 16, wherein said ovarian cancer is serous type, endometriod type, mucinous type, clear cell type, or transitional type.

18. The method of claim 15, wherein said patient has previously been treated surgically or hormonally for said cancer.

19. The method of claim 15, wherein said first sample is taken from said patient prior to being treated for said cancer.

20. The method of claim 15, wherein said second sample is taken from said patient after being treated for said cancer.

21. A method according to claim 15, wherein said sample is serum, blood plasma, ascites fluid, urine, vaginal secretion, or tissue biopsy.

22. A method according to claim 15, further comprising detecting the presence of HE4, SLPI or CA-125 in said patient.

23. A method of diagnosing a mullerian derived cancer in a subject comprising:
    detecting the presence of an Elafin polypeptide in a sample from the subject;

determining the level of the Elafin polypeptide in said sample to provide a test value; and comparing the test value to a standard value, wherein a test value above the standard value is indicative of a mullerian derived cancer.

24. The method of claim 23, wherein said test value is 2 fold higher than said standard value.

25. The method of claim 23, wherein said test value is 5 fold higher than said standard value.

26. The method of claim 23, wherein said test value is 10 fold higher than said standard value.

27. A method according to claim 23, wherein said sample is serum, blood plasma, ascites fluid, urine, vaginal secretion, or tissue biopsy.

28. A method according to claim 23, further comprising detecting the presence of HE4, SLPI or CA-125 in said patient.

29. A method of screening for the presence of ovarian cancer in a subject, comprising contacting a sample taken from said subject with an anti-Elafin antibody under conditions permitting said antibody to specifically bind an antigen in the sample to form an antibody-antigen complex;

determining the amount of antibody-antigen complex in the sample as a measure of the amount of antigen in the sample; and comparing the antigen level to a standard value, wherein an elevated level of the antigen in the sample indicates the presence of ovarian cancer.

30. The method of claim 29, wherein said subject has previously been treated surgically or hormonally for said cancer.

31. A method according to claim 29, wherein said sample is serum, blood plasma, ascites fluid, urine, vaginal secretion, or tissue biopsy.

32. The method of claim 29, wherein said subject is BRAC1 or BRAC2 positive.

33. A method according to claim 29, further comprising detecting the presence of HE4, SLPI or CA-125 in said sample.

* * * * *

UNITED STATES PATENT AND TRADEMARK OFFICE
CERTIFICATE OF CORRECTION

Page 1 of 1

PATENT NO.        : 8,486,648 B2
APPLICATION NO.   : 11/883103
DATED             : July 16, 2013
INVENTOR(S)       : Livingston et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1559 days.

Signed and Sealed this
Twelfth Day of November, 2013

Teresa Stanek Rea
*Deputy Director of the United States Patent and Trademark Office*

SEQUENCE LISTING

<160> NUMBER OF SEQ ID NOS: 6

<210> SEQ ID NO 1
<211> LENGTH: 117
<212> TYPE: PRT
<213> ORGANISM: Homo sapiens

<400> SEQUENCE: 1

| Met | Arg | Ala | Ser | Ser | Phe | Leu | Ile | Val | Val | Phe | Leu | Ile | Ala | Gly |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Thr | Leu | Val | Leu | Glu | Ala | Ala | Val | Thr | Gly | Val | Pro | Val | Lys | Gly | Gln |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Asp | Thr | Val | Lys | Gly | Arg | Val | Pro | Phe | Asn | Gly | Gln | Asp | Pro | Val | Lys |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

| Gly | Gln | Val | Ser | Val | Lys | Gly | Gln | Asp | Lys | Val | Lys | Ala | Gln | Glu | Pro |
|-----|-----|-----|-----|-----|-----|-----|-----|-----|-----|-----|-----|-----|-----|-----|-----|
|     |     | 50  |     |     |     |     | 55  |     |     |     |     | 60  |     |     |     |

| Val | Lys | Gly | Pro | Val | Ser | Thr | Lys | Pro | Gly | Ser | Cys | Pro | Ile | Ile | Leu |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Ile | Arg | Cys | Ala | Met | Leu | Asn | Pro | Pro | Asn | Arg | Cys | Leu | Lys | Asp | Thr |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Asp | Cys | Pro | Gly | Ile | Lys | Lys | Cys | Cys | Glu | Gly | Ser | Cys | Gly | Met | Ala |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Cys | Phe | Val | Pro | Gln |
|-----|-----|-----|-----|-----|
|     |     |     | 115 |     |

<210> SEQ ID NO 2
<211> LENGTH: 595
<212> TYPE: DNA
<213> ORGANISM: Homo sapiens

<400> SEQUENCE: 2

```
aggccaagct ggactgcata agattggta tggccttagc tcttagccaa acaccttcct      60
gacaccatga gggccagcag cttcttgatc gtggtggtgt tcctcatcgc tgggacgctg     120
gttctagagg cagctgtcac gggagttcct gttaaaggtc aagacactgt caaaggccgt     180
gttccattca atggacaaga tcccgttaaa ggacaagttt cagttaaagg tcaagataaa     240
gtcaaagcgc aagagccagt caaaggtcca gtctccacta gcctggctc ctgccccatt      300 atcttgatcc ggtgcgccat gttgaatccc ctaaccgct gcttgaaaga tactgactgc     360
ccaggaatca agaagtgctg tgaaggctct tgcgggatgg cctgtttcgt tccccagtga     420
gagggagccg gtccttgctg cacctgtgcc gtccccagag ctacaggccc catctggtcc     480
taagtccctg ctgccttcc ccttcccaca ctgtccattc ttcctcccat tcaggatgcc     540
cacggctgga gctgcctctc tcatccactt tccaataaag agttccttct gctcc          595
```

<210> SEQ ID NO 3
<211> LENGTH: 20
<212> TYPE: DNA
<213> ORGANISM: Artificial Sequence
<220> FEATURE:
<223> OTHER INFORMATION: Chemically Synthesized Primer

<400> SEQUENCE: 3

```
cggcttcacc ctagtctcag                                                 20
```

<210> SEQ ID NO 4
<211> LENGTH: 20
<212> TYPE: DNA

```
<213> ORGANISM: Artificial Sequence
<220> FEATURE:
<223> OTHER INFORMATION: Chemically Synthesized Primers

<400> SEQUENCE: 4
cctccttatc attgggcaga                                               20

<210> SEQ ID NO 5
<211> LENGTH: 18
<212> TYPE: DNA
<213> ORGANISM: Artificial Sequence
<220> FEATURE:
<223> OTHER INFORMATION: Chemically Synthesized Primer

<400> SEQUENCE: 5
acagagcctc gcctttgc                                                 18

<210> SEQ ID NO 6
<211> LENGTH: 20
<212> TYPE: DNA
<213> ORGANISM: Artificial Sequence
<220> FEATURE:
<223> OTHER INFORMATION: Chemically Synthesized Primer

<400> SEQUENCE: 6
aggatgcctc tcttgctctg                                               20
```